(12) United States Patent
Mortensen

(10) Patent No.: US 9,241,616 B1
(45) Date of Patent: Jan. 26, 2016

(54) SPECTRAL ILLUMINATION ATTACHMENT FOR DENTAL CAMERA

(71) Applicant: Steven Martin Mortensen, San Carlos, CA (US)

(72) Inventor: Steven Martin Mortensen, San Carlos, CA (US)

(*) Notice: Subject to any disclaimer, the term of this patent is extended or adjusted under 35 U.S.C. 154(b) by 0 days.

(21) Appl. No.: 14/251,526

(22) Filed: Apr. 11, 2014

Related U.S. Application Data

(60) Provisional application No. 61/812,025, filed on Apr. 15, 2013.

(51) Int. Cl.
| | | |
|---|---|---|
| *A61B 1/04* | (2006.01) | |
| *A61B 1/06* | (2006.01) | |
| *A61B 1/24* | (2006.01) | |
| *A61B 5/00* | (2006.01) | |
| *G03B 15/14* | (2006.01) | |

(52) U.S. Cl.
CPC ............. *A61B 1/0638* (2013.01); *A61B 1/043* (2013.01); *A61B 1/24* (2013.01); *A61B 5/0088* (2013.01); *A61B 5/742* (2013.01); *G03B 15/14* (2013.01)

(58) Field of Classification Search
USPC ............ 396/14, 16, 17; 348/45; 600/101, 109
See application file for complete search history.

(56) References Cited

U.S. PATENT DOCUMENTS

| | | | | |
|---|---|---|---|---|
| 3,896,463 | A * | 7/1975 | Laskey ......................... | 396/544 |
| 5,908,294 | A * | 6/1999 | Schick et al. .................. | 433/29 |
| 6,599,238 | B2 * | 7/2003 | Ooshima et al. .............. | 600/121 |
| 8,721,524 | B2 * | 5/2014 | Ichihashi et al. ............. | 600/110 |
| 2004/0236232 | A1 * | 11/2004 | Jonusauskas et al. ........ | 600/477 |
| 2011/0157457 | A1 * | 6/2011 | Mo et al. ....................... | 348/349 |

FOREIGN PATENT DOCUMENTS

JP          2006081842  A  *  3/2006

OTHER PUBLICATIONS

JP2006-081842 A Machine Translation available from JPO website.*

* cited by examiner

*Primary Examiner* — Minh Phan
(74) *Attorney, Agent, or Firm* — Thomas M. Freiburger

(57) ABSTRACT

An illumination attachment for an intraoral camera quickly attaches to the distal end of the camera and provides non-white illumination at a specific desired wavelength for diagnosing gum disease and tooth decay.

8 Claims, 5 Drawing Sheets

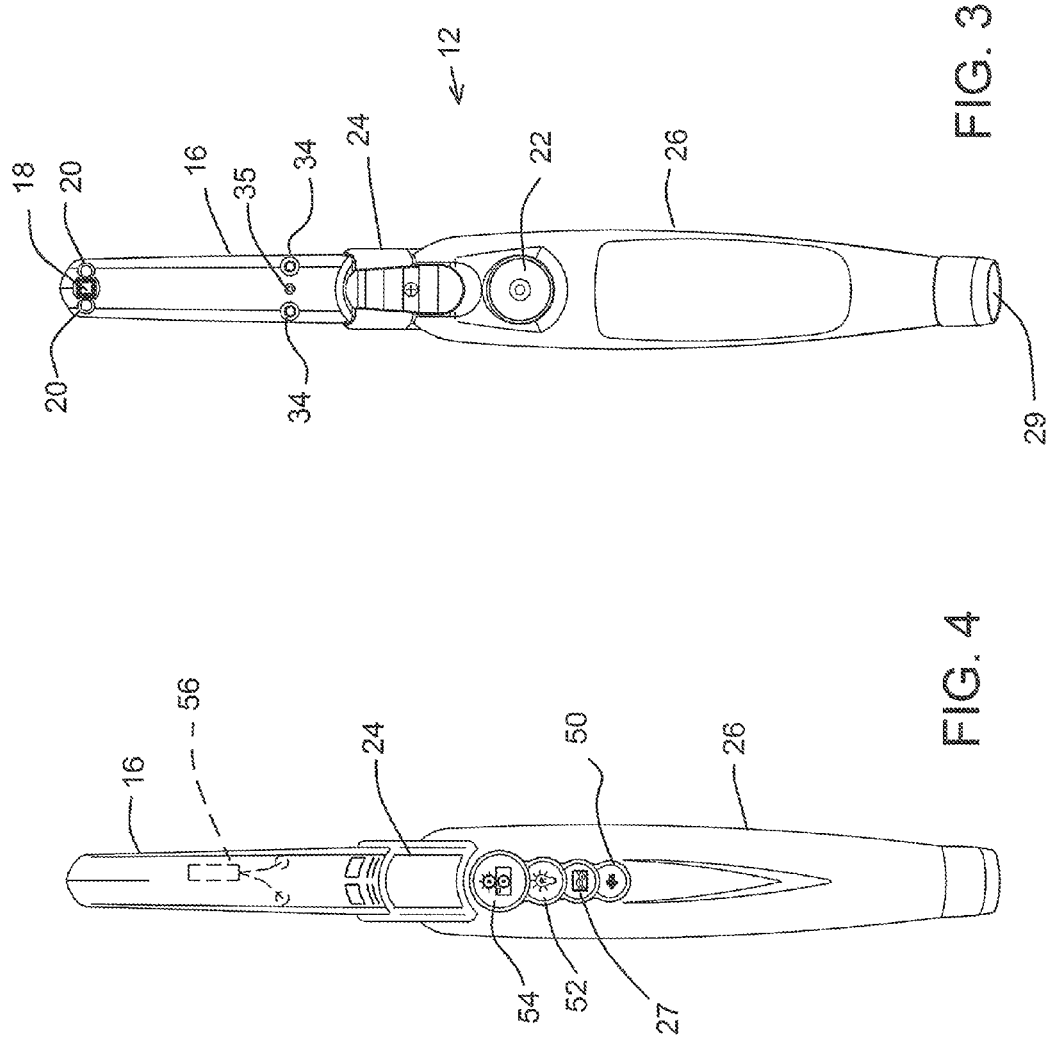

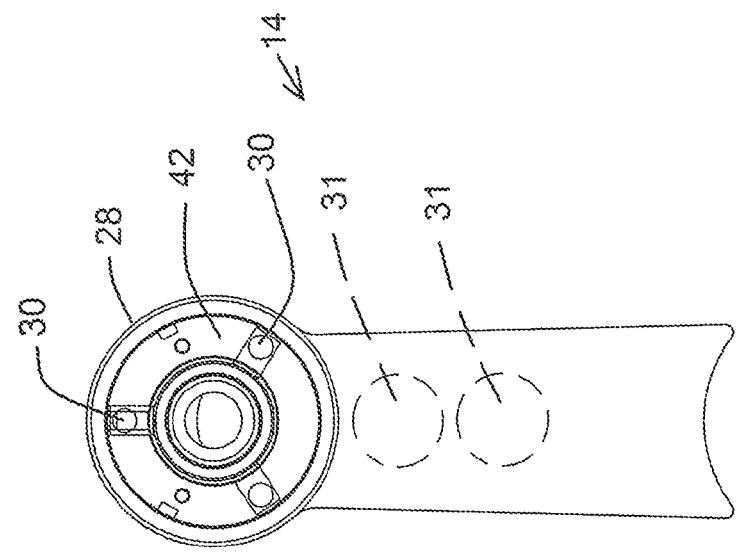
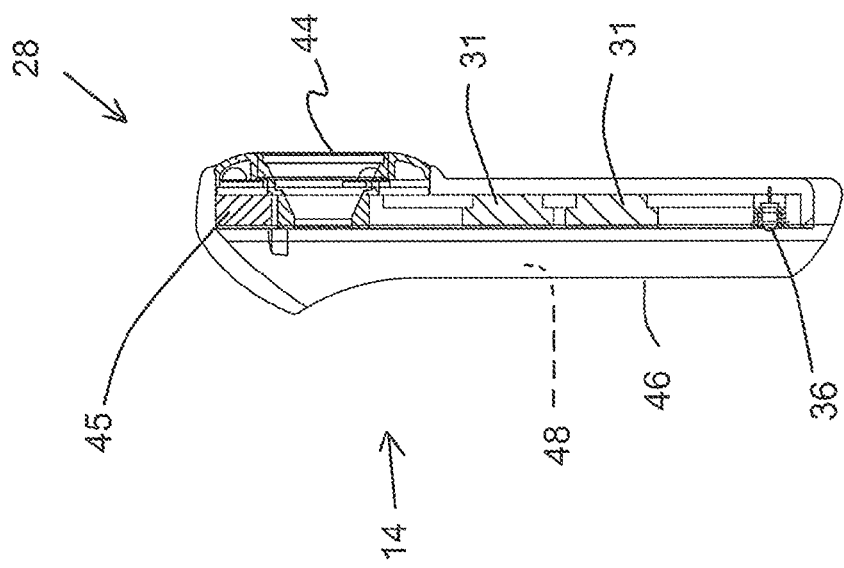
FIG. 5
FIG. 6

SPECTRAL ILLUMINATION ATTACHMENT FOR DENTAL CAMERA

This application claims benefit of provisional application Ser. No. 61/812,025, filed Apr. 15, 2013.

BACKGROUND OF THE INVENTION

The invention concerns dental equipment, and in particular relates to a spectral illumination device that attaches to an intraoral dental camera (IOC) enabling the camera to become a diagnostic cancer and/or caries detection device.

A basic intraoral dental camera handpiece consists of a hand held implement having an optical probe that extends on a wand out about four inches from the handle portion and views at a right angle using its own lighting. Focus is adjustable and images range from full face down to macros. The optical tip is heated for an anti-fog feature which is produced by controlling heat from the lighting elements.

Analytic scope devices are currently sold in the dental market for examinations and inspections for oral cancer. These devices provide for inspection but are not cameras.

With the current invention described below, a single implement can serve as an intraoral dental camera and simultaneously as a diagnostic device for cancer or caries.

SUMMARY OF THE INVENTION

The device of the invention is an attachment to an intraoral dental camera that enhances the evidence that is seen with the IOC. It expands the functions of an intraoral camera and adds the parameters of multiple spectrums of light, enabling the intraoral camera to become a diagnostic device to detect various cancers and tooth decay and caries. The lighting is unique in this attachment device and is the salient feature of what makes the invention uniquely advantageous. The use of filters, visible white light and a selected diagnostic light spectrum in the range from 200 nm to 700 nm are what make this attachment enable the intraoral camera to do what no other IOC can do, help identify oral cancers and other diseases.

The illumination attachment interfaces with the dental camera preferably using magnets located on the inside of the attachment to secure the attachment to the camera's nose tip. The camera has specifically located iron-containing metal pads inside to connect the two parts. A small battery can be located inside the attachment to power the diagnostic light, or if without battery, electrical contacts are provided on both the camera and the attachment. These power contacts preferably are live only if and when the magnetics from the attachment are in place. All power is provided by a USB port on the IOC, and the USB connection also typically provides the video images to a computer and monitor.

The basic advantage of the multi-spectral diagnostic camera attachment of the invention over standard available cancer scopes is that the invention enables either a dedicated IOC or almost any standard IOC on current market to become a diagnostic imaging tool with the simplicity of attaching this illumination device to the camera. It also easily detaches so that the camera can again operate simply as a standard intraoral camera. The increased utility of the IOC now includes the standard use as an intraoral camera using its own white light for viewing full color images (typical use for an IOC), and the new ability to become a diagnostic imaging tool using a different light wavelength useful for that purpose.

The illumination attachment is powered by either a remote power supply (from the camera) or an onboard rechargeable battery. When needed, the user simply attaches the illumination unit to the dental camera handpiece with the magnetic coupling and then switches the power on via the camera. If used with a standard camera the user will turn off the camera's normal lighting system and then view the oral cavity using the spectral attachment's lighting system. If used with an exclusive, dedicated IOC, then the user will additionally switch on the spectral examination mode on the camera which will engage the addition of the electronic imagery enhancements of the camera that automatically work in accordance with the light spectrums and direct and/or reverse imagery to better amplify visual auto-fluorescence and excitation effects.

Exclusive or dedicated camera description: The exclusive intraoral dental camera is a USB device that is also a UVC (USB Video Class) device. It is simple to use and by using Microsoft's UVC platform as its video source the user can easily plug it into any computer and immediately operate the camera without the need of installing drivers. The exclusive IOC also has a specific mode switch that works in conjunction with the illumination attachment. Its processor and light control system help enhance the visual effects and help perfect images to see a clearer picture with greater penetration into tissues and dentin. With this combination of the spectral illumination attachment and the exclusive, dedicated camera, it can now use the above described features and wavelengths of lighting to auto-fluoresce tissues inside the oral cavity and better detect oral diseases. The practitioner can slip on the diagnostic illumination attachment and project a different wavelength or spectrum of light on the patient's teeth and tissues.

The invention achieves a versatile multi-function intraoral dental implement, useful as a camera, a disease-detecting scope or both simultaneously. These and other objects, advantages and features of the invention will be apparent from the following description of a preferred embodiment, considered along with the accompanying drawings.

DESCRIPTION OF THE DRAWINGS

FIG. 3 is an elevation view showing the front of the camera.

FIG. 4 is a rear elevation view showing the back side of the camera.

FIGS. 5 and 6 are frontal elevation and side sectional views of the attachment.

DESCRIPTION OF PREFERRED EMBODIMENTS

Figure 1:
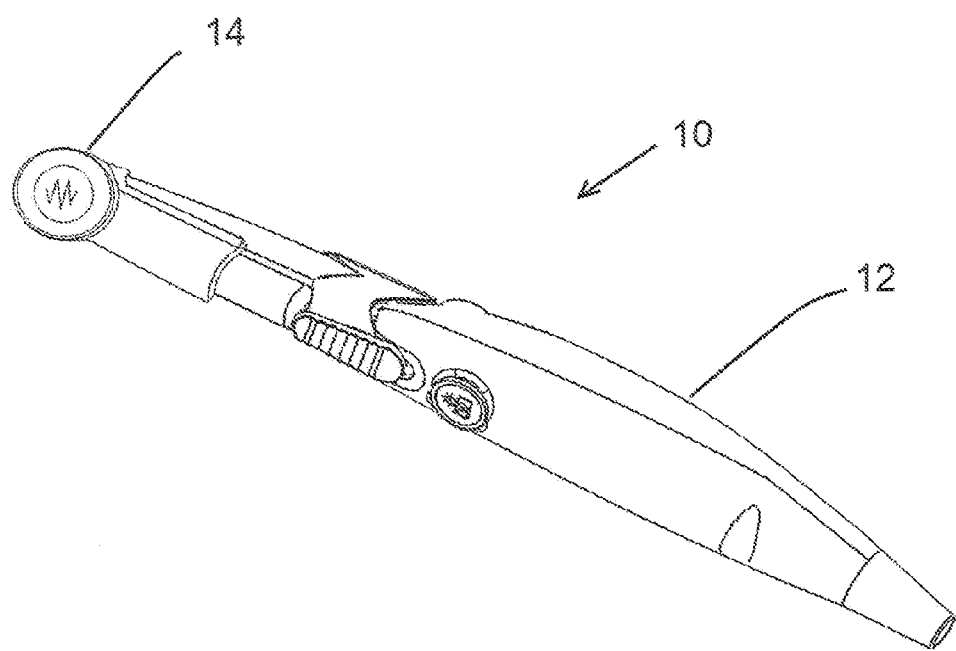
FIG. 1 is a perspective view showing a intraoral camera in combination with a multi-spectral illumination attachment, secured on the distal end of the camera.
Figure 2:
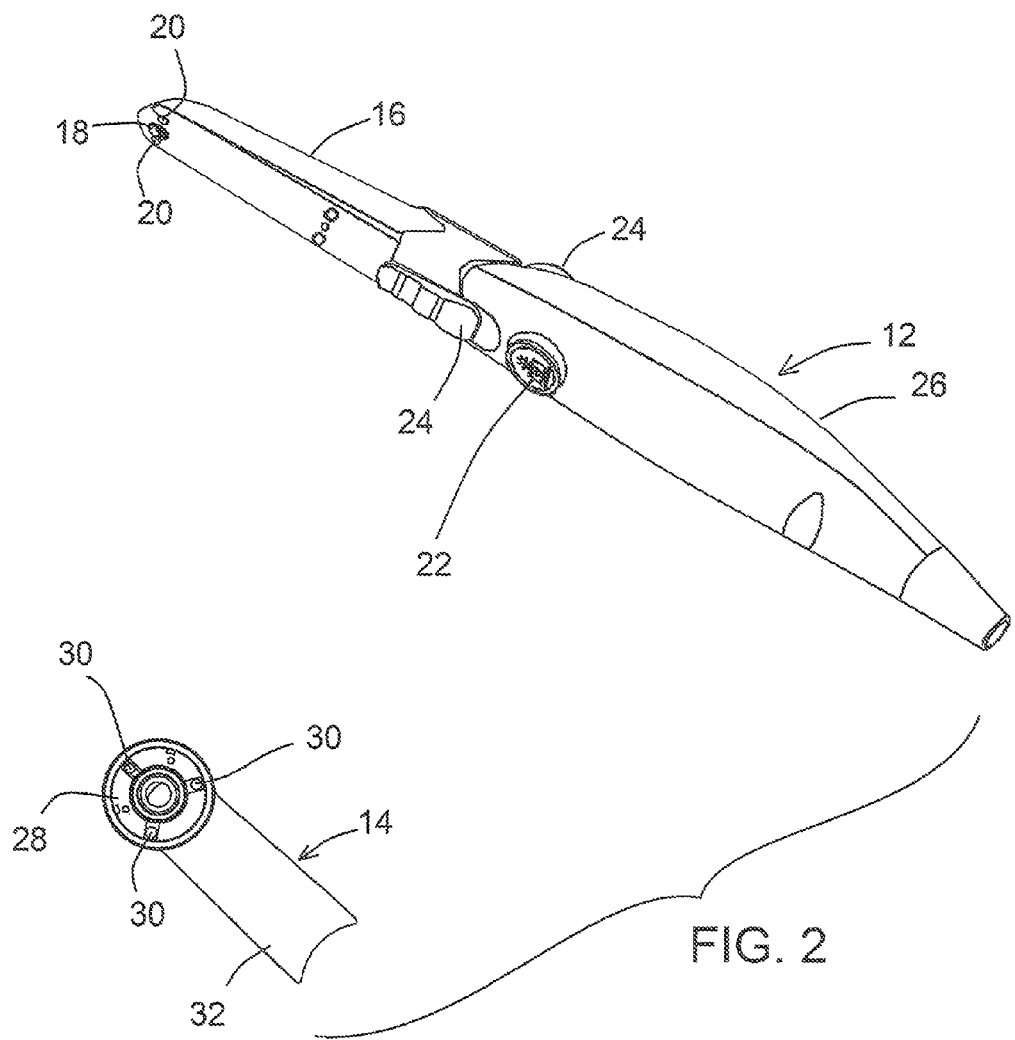
FIG. 2 is a perspective view showing the attachment separated from the camera.

In the drawings, FIG. 1 shows an embodiment of the invention, the device 10 comprising a connected intraoral camera 12 and illumination attachment 14. FIG. 2 shows the camera 12 and the attachment 14 separately.

The camera 10 can be the IMAGEMASTER intraoral camera produced by Imagin Systems of San Carlos, Calif.

The intraoral camera has a CMOS image detector, and the device plugs into a computer via USB cable, for a dentist to view teeth and tissue, moving the distal wand 16 of the camera device as he views a moving image on a computer monitor. A camera imaging window is near the tip of the wand, at 18, positioned adjacent to and essentially between two LED light sources 20 (pillow LEDs) that produce white light. The actual CMOS image detector is not at the tip of the wand but deeper down the length of the camera device, with a right-angle prism (not shown) just inside the image window directing light of the viewed area down to the CMOS detector. The camera device 12 typically has an image capture button on the handle, as at 22, and a slide focus adjustment at 24, usable from either side of the device's handle 26. The handle also has a mode button 27 (FIG. 4) which can be used to adjust the type of imaging. The camera includes firmware and a processor for adjusting the light output and mode of imaging, including grayscale and translucency mode, as controlled by the mode button.

The remaining drawings also show the camera 12, as well as the attachment 14, in other views. In FIG. 3 a USB connector port is at 29 at the bottom of the handle. The capture button 22, focus slider 24, and LEDs 20 and imaging window 18 are also seen in that frontal view.

The invention encompasses primarily the spectral illumination attachment 14, but also the camera 12 in slightly modified form, and the combination of the camera with the illumination device 14 attached. FIGS. 1, 2 and 5 show the attachment 14 with a preferably circular head 28 that carries three or four LED light sources 30, three such light sources being shown at equal-angular positions on the head in these views. The attachment 14 has a stem portion 32 that slides onto and closely fits on the distal wand 16 of the camera device. When the attachment is fitted onto the distal end of the camera device, as can be envisioned from the perspective view of FIG. 2 and also FIGS. 5-8, the tip of the wand with the imaging window 18 slides up into the head 28 so that the imaging window 18 is located essentially centrally within the circular head, with the LED illumination sources 30 surrounding the imaging window. The two components are attached together preferably using magnets, with permanent magnets 31 (shown in the sectional view of FIG. 6) being included in the stem portion 32 of the attachment and ferrous metal being included at corresponding locations in the wand 16 of the camera device.

Figure 7:
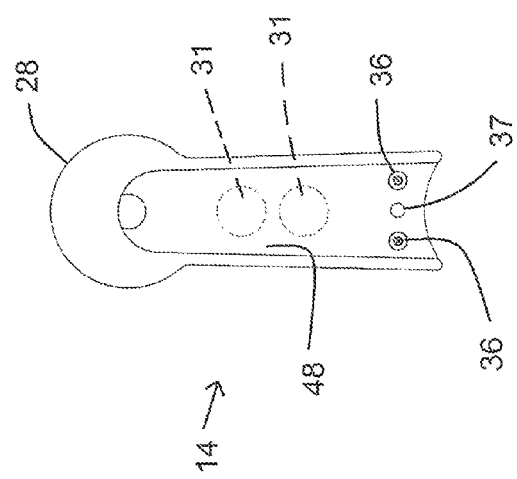
FIG. 7 is a rear view of the attachment.

Further, the modified intraoral camera 12 preferably has a pair of electrical contacts 34 at positions to be engaged by electrical contacts 36 on the attachment, seen in FIG. 7 and shown in dashed lines in FIG. 5. Between the contacts 36 is preferably included a pin port 37 for a locating pin 35 on the camera. When the attachment is secured in place on the camera, these contacts 34, 36 conduct electrical current to activate the LEDs 30 on the illumination attachment. This contact can also have the effect of switching off power to the IOC's own pair of illumination LEDs 20, or the camera device can include an internal switch, triggered by the magnet of the attachment, to turn off power to the two LEDs 20.

The spectral illumination attachment 14 preferably has specifically selected LEDs that produce a specific desired wavelength which will make certain conditions and diseases visible to the practitioner, and which will cause auto-fluorescing of features to reveal their presence. One preferred wavelength for the light emitted from the attachment is about 460 nm, preferably in the blue range of 450 nm to 470 nm. However, filters to adjust color could be placed over the LEDs in production of the attachment if desired. In a variation of the invention, the circular head 28 could have a manually rotatable adjustment wheel enabling the practitioner to select different filter enhancements to fine-tune wavelength, if needed, by positioning different filters in front of the LEDs. Details of such an embodiment are not shown, but the head includes a circular area 42 surrounding the central opening or window 29, and this could be an open disc retained in place by the surrounding structure so as to be manually rotatable when desired.

FIG. 6 also shows a central filter window 44 on the attachment's head 28, this filter being to reduce blue in the images detected by the camera. Further, FIG. 6 indicates a heat sink 45, such as of aluminum, to draw heat from the LEDs and to provide anti-fog protection for viewing.

The illumination attachment can be open at its back side 46 as shown in FIGS. 6 and 7, forming a sort of cupped sleeve channel 48 for receipt of the IOC wand, or it could be formed fully envelop the distal wand 16 of the camera.

FIG. 4, showing the back side of the IOC, reveals various controls. The mode selection button is at 27, for selecting black and white, translumination, etc., and also a cancer diagnostic mode for operating the camera's processor to present the image, as illuminated by the attachment 14, as desired. Also seen is a button 50 for on-screen arrow and mirror orientation, a light brightness adjustment/ON/OFF button 52 (which operates the attachment's lights when the attachment is present) and a top capture button 54 for capturing images. Note that some of these functions could be operable by one or more foot pedals if desired, via the USB connection.

FIG. 4 also shows in dashed lines at 56 the internal device referred to above that senses a magnetic field of the attachment's magnets and switches off power to the IOC's LEDs 20.

Figure 8:
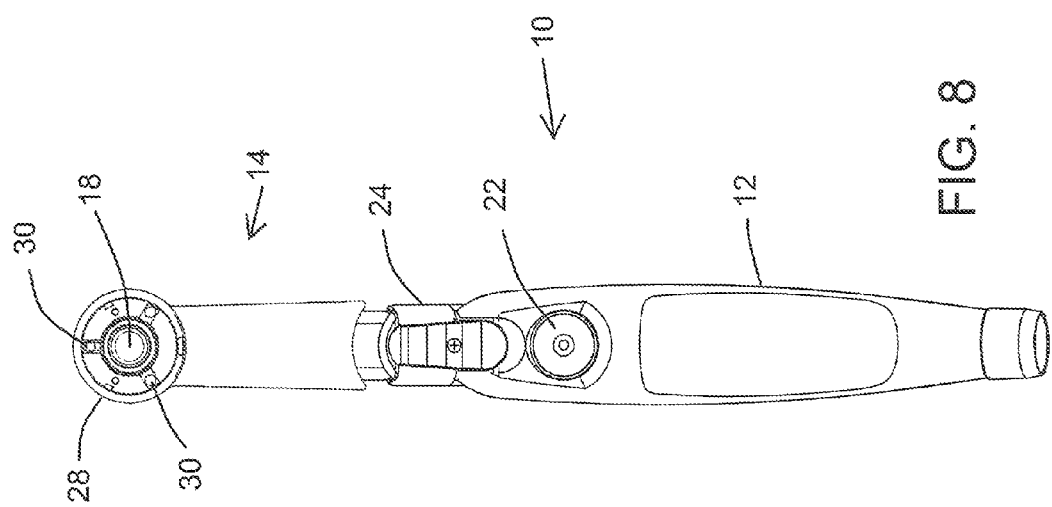
FIG. 8 is a front elevation view showing the IOC with attachment.

FIG. 8 shows the combined IOC/illumination attachment with the LEDs 30 of the attachment surrounding the camera's imaging window 18 projecting light of the desired wavelength via filtration.

The intraoral camera, referred to above as being a variant of the IMAGEMASTER camera of Imagin Systems, cooperates with the attachment 14 by including at least the following new features: the magnetic pickup switching device 56; the ferrous metal contained within the IOC wand 16 for attraction by the attachment magnets; the electrical contacts 34 and locating pin 35 on the distal wand; and programming of the internal processor of the IOC for presenting spectrally illuminated images in different modes as described above (translumination, cancer diagnostic mode, etc.).

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. An intraoral inspection and diagnostic device, comprising:
    an elongated intraoral camera including a proximal handle and a distal wand extending from the handle, with an imaging window at a remote end of the distal wand, the imaging window directing an image to an image sensor in the camera, and the distal wand having an onboard LED light source adjacent to the imaging window for illuminating tissue, with the intraoral camera having a power supply for powering the onboard LED light source and an on/off/brightness control switch to control power to the onboard LED light source,
    a spectral illumination attachment securable to and removable from the distal wand of the intraoral camera, the attachment being contoured to fit closely on the distal wand of the intraoral camera, the attachment having a distal LED light source positioned to be adjacent to the imaging window so as to direct light in the direction of camera viewing when the attachment is secured on the wand, and the distal LED light source producing non-white light in a specific wavelength range capable of diagnostic imaging, and the distal wand of the intraoral camera having a pair of electrical contacts and the illumination attachment having a pair of mating contacts such that when the attachment is slipped over the distal wand of the camera the contacts mate to provide power from the intraoral camera to the distal LED light source of the attachment, the securing of the attachment to the distal wand also being effective to transfer control of the on/off/brightness switch to the distal LED light source of the attachment, whereby the intraoral camera can be used in a normal function of imaging dental features and tissues without the attachment, and with the attachment the combined intraoral camera and attachment can be used to diagnose teeth and surrounding tissue for various cancers, tooth decay and other diseases, as viewable on a monitor, with the distal LED light source controlled by the on/off/brightness control switch on the intraoral camera, and diagnostic images can be recorded.

2. The device of claim 1, wherein the illumination attachment includes a distal head and the distal LED light source comprises at least three LEDs, the distal head having a central opening in which the imaging window of the intraoral camera is positioned, surrounded by the LEDs.

3. The device of claim 1, wherein the distal LED light source produces light at about 450 nm to 470 nm.

4. The device of claim 1, wherein the illumination attachment is retained to the distal wand of the camera by magnets in the attachment, attracted to ferrous metal in the distal wand.

5. The device of claim 1, wherein the distal LED light source produces light in a wavelength range that causes autofluorescence to excite oral tissue for detecting cancer and tooth caries.

6. The device of claim 1, wherein the imaging window of the camera contains a prism to reflect an image to the image sensor, which is located at a remote position from the prism inside the intraoral camera.

7. The device of claim 4, wherein the distal wand of the camera includes a magnetic pickup switch to switch off power to the camera's onboard LED light source when the illumination attachment is secured onto the distal wand.

8. The device of claim 1, wherein the securing of the attachment to the distal wand is further effective to switch off power to the camera's onboard LED light source when the illumination attachment is secured onto the distal wand.

* * * * *